US00PP27532P3

(12) United States Plant Patent
Zaiger et al.

(10) Patent No.: US PP27,532 P3
(45) Date of Patent: Jan. 10, 2017

(54) PEACH TREE NAMED 'SNOW BABY'

(50) Latin Name: *Prunus persica*
Varietal Denomination: Snow Baby

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 1038 days.

(21) Appl. No.: 13/506,164

(22) Filed: Apr. 2, 2012

(65) Prior Publication Data

US 2013/0263341 P1 Oct. 3, 2013

(51) Int. Cl.
*A01H 5/08* (2006.01)

(52) U.S. Cl.
USPC ..... Plt./195
CPC ..... *A01H 5/0868* (2013.01)

(58) Field of Classification Search
USPC ..... Plt./195
See application file for complete search history.

*Primary Examiner* — Susan McCormick Ewoldt

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. The tree being a regular and productive bearer of large size, white flesh fruit.
2. The tree with vigorous, upright growth.
3. Producing fruit with an attractive dark red skin color.
4. Fruit with good flavor and eating quality with a mild, sweet, sub-acid flavor.
5. Fruit with good storage and shipping quality.

1 Drawing Sheet

Botanical designation: *Prunus persica.*
Variety denomination: 'Snow Baby'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

Prior Varieties

Among the existing varieties of peach trees, which are known to us, and mentioned herein, 'Sugar Lady' Peach (U.S. Plant Pat. No. 7,532), 'Rich Lady' Peach (U.S. Plant Pat. No. 7,290), 'Country Sweet' Peach (U.S. Plant Pat. No. 11,090), 'Zee Lady' Peach (U.S. Plant Pat. No. 5,832), 'Sweet Gem' Peach (U.S. Plant Pat. No. 7,952), 'Zee Diamond' Peach (U.S. Plant Pat. No. 9,673), 'Super Rich' Peach (U.S. Plant Pat. No. 9,860), 'Amparo' Peach (U.S. Plant Pat. No. 6,472), 'Spring Snow' Peach (U.S. Plant Pat. No. 9,883), 'Snow Fox' Peach (U.S. Plant patent application Ser. No. 14/544,568), and the proprietary non-patented peach seedling selections '196LT639', '59Z480' and '35M358'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. from seed of a first generation cross between our two proprietary non-patented peach seedling selections with field identification numbers '196LT639' and '35M358'. The seed parent '196LT639' (non-patented) originated from crosses between 'Sugar Lady' Peach (U.S. Plant Pat. No. 7,532), 'Rich Lady' Peach (U.S. Plant Pat. No. 7,290) and the proprietary seedling selection '59Z480' peach (non-patented). The pollen parent '35M358' (non-patented) originated from crosses between the following varieties; 'Sweet Gem' Peach (U.S. Plant Pat. No. 7,952), 'Zee Diamond' Peach (U.S. Plant Pat. No. 9,673), 'Super Rich' Peach (U.S. Plant Pat. No. 9,860), 'Country Sweet' Peach (U.S. Plant Pat. No. 11,090), 'Zee Lady' Peach (U.S. Plant Pat. No. 5,832) and 'Amparo' Peach (U.S. Plant Pat. No. 6,472). A large number of these first generation seedlings were grown and budded on older 'Nemaguard' Rootstock (non-patented) to accelerate rapid fruit production for evaluation. Under close and careful observation, one such seedling, which is the present variety, exhibited desirable tree and fruit characteristics and was selected in 2007 for further asexual propagations and commercialization.

ASEXUAL REPRODUCTION OF THE VARIETY

In 2007 asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of peach tree (*Prunus persica*) is of large size, vigorous, upright growth and a productive and regular bearer of large size, clingstone fruit with mild, sweet, sub-acid flavor and good eating quality. The fruit is further characterized by having an attractive dark red skin color, firm, white flesh and being relatively uniform in size throughout the tree. In comparison to the proprietary seed parent '196LT639' peach (non-patented) the fruit of the new variety is larger in size and approximately 30 days later in maturity. In comparison to the proprietary pollen parent '35M358' peach (non-patented) the fruit of the new variety has white compared to yellow flesh, a more attractive red skin color and is approximately 4 days earlier in maturity. In comparison to the commercial variety 'Spring Snow' Peach (U.S. Plant Pat. No. 9,883) the fruit of the new variety has a more attractive, darker red skin color and is approximately 9 days later in maturity. In comparison to 'Snow Fox' Peach (U.S. Plant patent application Ser. No. 14/544,568), which is the sister sibling of the present variety, with both being grown together on original mother tree on separate scaffolds and having the exact same cultural conditions, we found these differences; the fruit of the new variety being 4 days later in maturity, being slightly smaller in size, having a darker red skin color, and its flowers blooming 2 days later. Having a higher chilling requirement of approximately 50 hours allowing the new variety to be planted in more northern growing areas that require more chilling hours. The new variety has more areas of exposed ground color on the skin giving it a speckled appearance that 'Snow Fox' Peach (U.S. Plant patent application Ser. No. 14/544,568) does not exhibit.

DESCRIPTION OF THE PHOTOGRAPH

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of peach tree, its flowers, foliage and ,fruit, as based on observations of 5 year old specimens grown near Modesto, Calif., with color in accordance with Munsell Book of Color.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters in height the first growing season. Varies with soil type, fertility and climatic conditions.

*Form*.—Upright, usually pruned to vase shape.

*Branching habit*.—Upright, crotch angle approximately 30°, increases with heavy crop load.

*Productivity*.—Productive, fruit thinning and spacing necessary for desired market size. Fruit set varies with climatic conditions during bloom season.

*Bearer*.—Regular, adequate fruit set 3 consecutive years. No alternate bearing observed.

*Fertility*.—Self fertile.

*Density*.—Medium dense, usually pruned to vase shape to allow more sunlight to center of tree to enhance fruit color and health of fruit wood.

*Hardiness*.—Hardy in all stone fruit growing areas of California. Tree grown in USDA Hardiness Zone 9. Winter chilling requirement approximately 600 hours at or below 45° F.

Trunk:

*Size*.—Medium. Average circumference 55.9 cm at 20.3 cm above ground on a 5 year old tree.

*Stocky*.—Medium stocky.

*Texture*.—Medium shaggy, roughness increases with age.

*Color*.—Varies from 5Y 5/2 to 5Y 4/2.

Branches:

*Size*.—Medium. Average circumference 10.9 cm at 1.0 meter above ground. Crotch angle approximately 30°, increases with heavy crop load.

*Surface texture*.—New growth relatively smooth. Mature growth medium rough, roughness increases with age of growth.

*Lenticels*.—Large. Average number 21 in a 25.8 sq cm section. Average length 4.1 mm. Average width 1.9 mm. Color varies from 10YR 6/8 to 10YR 5/8.

*Color*.—New growth varies from 5GY 6/6 to 5R 3/8 where exposed to the sun. Mature growth varies from 5YR 5/2 to 5YR 2/4, varies with age of growth.

Leaves:

*Size*.—Large. Average length 133.6 mm. Average width 41.1 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slightly indented over midrib and leaf veins. Lower surface relatively smooth except for small ridges created by midrib and pinnate venation. Both surfaces glabrous.

*Petiole*.—Average length 10.7 mm. Average width 1.5 mm. Color 5GY 4/8. Longitudinally grooved. Surface — glabrous.

*Glands*.—Type — reniform. Size — medium to large. Average length 1.1 mm. Average diameter 0.9 mm. Average number 3, varies from 2 to 4. Located primarily on base of leaf blade and upper portion of petiole. Color varies from 2.5GY 6/6 to 5GY 5/6.

*Stipules*.—Average length 7.8 mm. Average number 2. Margin — pectinate. Color 5GY 5/6.

*Color*.—Upper surface varies from 10GY 3/4 to 7.5GY 3/4. Lower surface varies from 10GY 4/4 to 7.5GY 4/4. Midvein color varies from 5GY 8/4 to 2.5GY 6/4.

Flower buds:

*Size*.—Large. Average length 18.2 mm. Average diameter 11.3 mm.

*Hardiness*.—Hardy with respect to California winters.
*Density*.—Medium.
*Form*.—Plump, conical, becoming elongated before opening.
*Pedicel*.—Average length 4.7 mm. Average width 1.2 mm. Color varies from 2.5GY 5/6 to 5GY 6/6. Surface glabrous.
*Color*.—Varies from 7.5RP 7/8 to 5RP 7/10.

Flowers:
*Blooming period*.—Date of First Bloom Feb. 27, 2011. Date of Petal Fall Mar. 7, 2011, varies slightly with climatic conditions.
*Size*.—Large, showy. Average height 19.9 mm. Average diameter 32.2 mm.
*Petals*.—Normally 5, alternately arranged to sepals. Size — large. Average length 17.9 mm. Average width 18.7 mm. Form — orbicular. Arrangement — overlapping. Petal apex — rounded. Petal base — rounded to somewhat truncated. Margin — sinuate. Both upper and lower surfaces glabrous. Color varies from 2.5RP 9/2 to 5RP 7/8, fades with age of flower. Both upper and lower surfaces glabrous.
*Sepals*.—Normally 5, alternately arranged to petals. Size — large. Average length 5.9 mm. Average width 5.7 mm. Shape — triangular, apex rounded. Margin — entire. Upper surface- glabrous. Lower surface — pubescent. Color — upper surface varies from 2.5GY 6/8 to 7.5R 2/6. Lower surface varies from 2.5R 2/8 to 10Y 6/6.
*Stamens*.—Average number per flower 40. Average filament length 15.2 mm. Filament color varies from N 9.5/(white) to 5RP 8/4, depending on age of flower. Anther color varies from 7.5R 2/8 to 5R 3/10. On average, the stamens are below the height of the petals.
*Pollen*.—Self fertile. Color varies from 2.5Y 8/14 to 5Y 8.5/10.
*Pistil*.—Normally one. Surface — pubescent. Average length 16.7 mm. Position of stigma even with anthers. Ovary — pubescent. Color varies from 7.5Y 8.5/10 to 5Y 8.5/8.
*Fragrance*.—Heavy aroma.
*Color*.—Varies from 2.5RP 9/2 to 5RP 7/8.
*Number flowers per flower bud*.—One.
*Pedicel*.—Average length 4.7 mm. Average width 1.3 mm. Color varies from 10Y 7/8 to 2.5GY 7/6.

Fruit:
*Maturity when described*.—Firm ripe and ready for consumption.
*Date of first picking*.—Jun. 4, 2011.
*Date of last picking*.—Jun. 11, 2011, varies slightly with climatic conditions.
*Size*.—Large. Average diameter axially 59.4 mm. Average transversely in suture plane 73.3 mm. Average weight 201.6 grams, varies slightly with fertility of the soil, amount of thinning and climatic conditions.
*Form*.—Globose.
*Suture*.—Nearly smooth, extends from base to apex.
*Ventral surface*.—Very slightly lipped, nearly smooth.
*Apex*.—Slightly retuse.
*Base*.—Varies from flat to slightly retuse.
*Stem cavity*.—Rounded to slightly elongated in suture plane. Average depth 6.9 mm. Average diameter 9.1 mm.

Stem:
*Size*.—Medium. Average length 10.9 mm. Average diameter 4.0 mm.
*Color*.—Varies from 2.5GY 6/8 to 2.5GY 5/8.

Flesh:
*Ripens*.—Evenly.
*Texture*.—Firm, meaty.
*Fibers*.—Few, small, tender.
*Firmness*.—Good, comparable to other commercial varieties.
*Aroma*.—Slight.
*Amydgalin*.—Undetected.
*Eating quality*.—Good.
*Flavor*.—Good, mild, sweet, sub-acid.
*Juice*.—Moderate amount, enhances flavor.
*Acidity*.—Not available.
*Brix*.—Average Brix 11.2°, varies slightly with amount of fruit per tree and climatic conditions.
*Color*.—Varies from 10Y 9/1 to 7.5Y 9/2. The anthocyanin coloration next to the skin and the slight bleeding into the flesh near the stone varies from 2.5R 5/6 to 2.5R 5/8.
*Pit cavity*.—Average length 33.0 mm. Average width 25.0 mm. Average depth 11.0 mm. Color varies from 10Y 8.5/4 to 2.5GY 7/4.

Skin:
*Thickness*.—Medium.
*Surface*.—Smooth.
*Pubescence*.—Moderate amount, short in length.
*Tendency to crack*.—None.
*Color*.—Ground color varies. from 2.5Y 9/2 to 2.5Y 8.5/2. Overspread with 5R 3/4 to 2.5R 3/4.
*Tenacity*.—Tenacious to flesh.
*Astringency*.—Undetected.

Stone:
*Type*.—Clingstone, strong adherence to flesh.
*Size*.—Large. Average length 32.1 mm. Average width 23.9 mm. Average thickness 20.0 mm.
*Form*.—Ovoid.
*Base*.—Flat.
*Apex*.—Pointed. Average length 2.7 mm.
*Surface*.—Pitted throughout, pits vary from round to elongated.
*Sides*.—Unequal, one side extending further from suture plane.
*Ridges*.—Relatively smooth, extending from base to apex.
*Tendency to split*.—None.
*Color*.—Varies from 7.5YR 7/6 to 10YR 7/2 when dry. Anthocyanin coloration varies from 2.5R 4/8 to 2.5R 4/10 when first exposed from the flesh.

Kernel:
*Size*.—Large. Average length 15.9 mm. Average width 10.8 mm. Average depth 6.2 mm.
*Form*.—Ovoid.
*Viability*.—Viable, complete embryo development.
*Skin*.—Color varies from 7.5Y 9/4 to 10Y 9/2.

Use: Dessert.
*Market*.—Local and long distance.

Keeping quality: Good, held firm in cold storage at 38° to 42° F. for 3 weeks without internal breakdown of flesh or appreciable loss of flavor.

Shipping quality: Good, minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices. The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

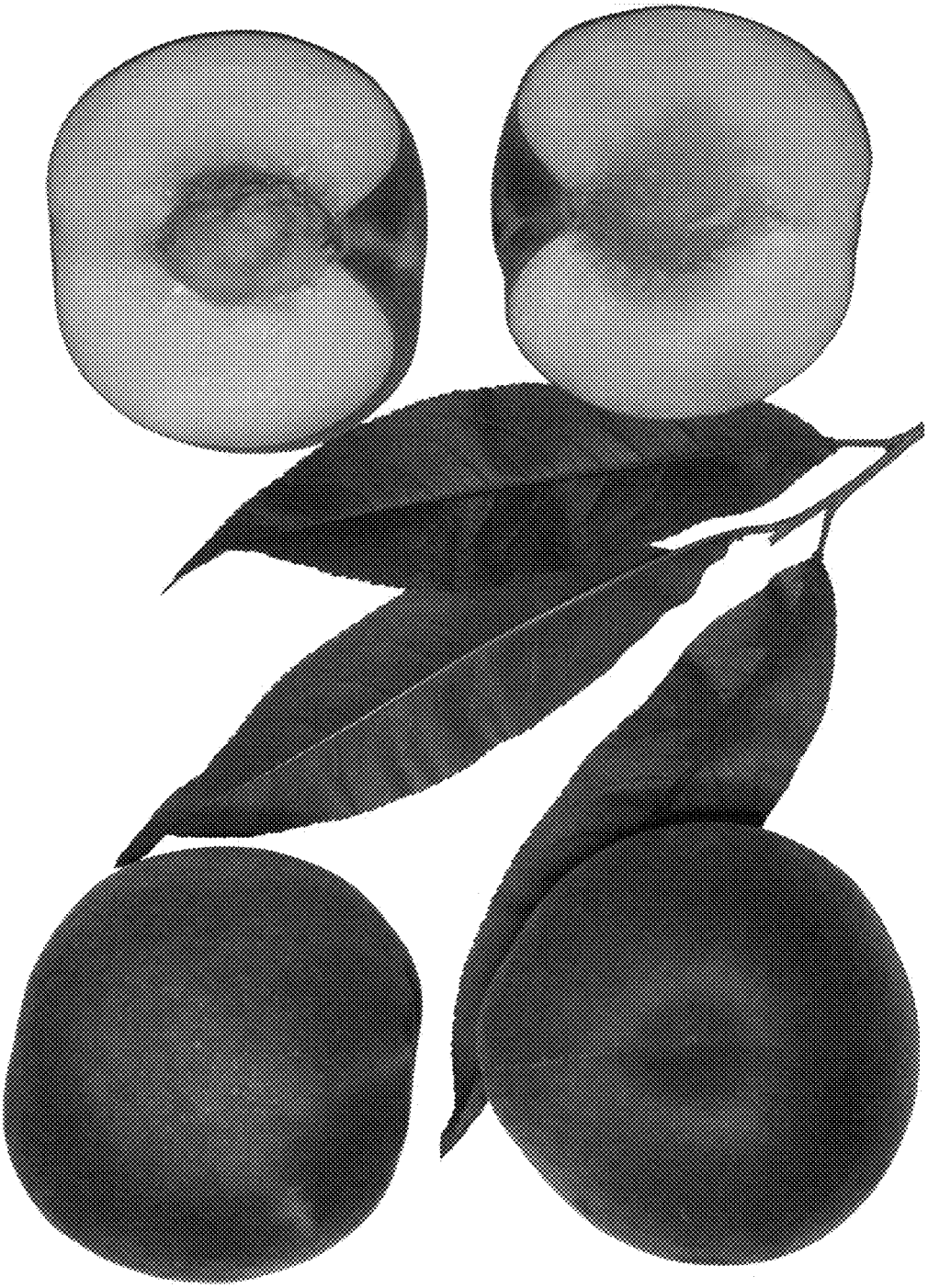

* * * * *